(12) United States Patent
Culver et al.

(10) Patent No.: US 9,480,425 B2
(45) Date of Patent: Nov. 1, 2016

(54) TASK-LESS OPTICAL MAPPING OF DYNAMIC BRAIN FUNCTION USING RESTING STATE FUNCTIONAL CONNECTIVITY

(75) Inventors: Joseph P. Culver, Webster Groves, MO (US); Brian R. White, Clayton, MO (US); Bradley L. Schlaggar, St. Louis, MO (US); Abraham Z. Snyder, St. Louis, MO (US); Marcus E. Raichle, Warson Woods, MO (US); Michael D. Fox, St. Louis, MO (US); Justin L. Vincent, Somerville, MA (US)

(73) Assignee: WASHINGTON UNIVERSITY, St. Louis, MO (US)

( * ) Notice: Subject to any disclaimer, the term of this patent is extended or adjusted under 35 U.S.C. 154(b) by 460 days.

(21) Appl. No.: 12/425,743

(22) Filed: Apr. 17, 2009

(65) Prior Publication Data

US 2009/0292210 A1    Nov. 26, 2009

Related U.S. Application Data

(60) Provisional application No. 61/045,855, filed on Apr. 17, 2008.

(51) Int. Cl.
| | | |
|---|---|---|
| *A61B 6/00* | (2006.01) | |
| *A61B 5/1455* | (2006.01) | |
| *A61B 18/22* | (2006.01) | |
| *A61B 5/00* | (2006.01) | |

(52) U.S. Cl.
CPC ......... *A61B 5/14553* (2013.01); *A61B 5/4064* (2013.01); *A61B 5/0042* (2013.01); *A61B 5/0059* (2013.01); *A61B 2018/2261* (2013.01); *A61B 2562/0233* (2013.01); *A61B 2562/046* (2013.01)

(58) Field of Classification Search
CPC .................. A61B 5/14553; A61B 2018/2261
USPC ...... 250/341.8; 356/432; 600/310, 312, 322, 600/323, 407, 410, 426, 473, 476; 700/117
See application file for complete search history.

(56) References Cited

U.S. PATENT DOCUMENTS

| | | |
|---|---|---|
| 3,668,634 A | 6/1972 | Kruklitis |
| 5,215,095 A | 6/1993 | Macvicar et al. |

(Continued)

FOREIGN PATENT DOCUMENTS

| | | |
|---|---|---|
| EP | 1329700 A | 7/2003 |
| WO | WO 2006/071891 A2 * | 6/2006 |

OTHER PUBLICATIONS

F.S. Azar et al. (2007) "Standardized platform for coregistration of nonconcurrent diffuse optical and magnetic resonance breast images obtained in different geometries" Journal of Biomedical Optics 12(5), pp. 051902.1-051902.14.*

(Continued)

*Primary Examiner* — Serkan Akar
(74) *Attorney, Agent, or Firm* — Armstrong Teasdale LLP

(57) ABSTRACT

A method for utilizing an optical system for mapping brain function includes determining a time series of light intensity measurements for spatially distributed source and detector pairs, receiving light measurements over a period of time, and producing at least one map of a respective strength of each of a plurality of temporal correlations, wherein the temporal correlations are based on the time series of the spatially distributed source and detector pairs and the light measurements.

17 Claims, 12 Drawing Sheets

(56) References Cited

U.S. PATENT DOCUMENTS

| | | | |
|---|---|---|---|
| 5,632,276 | A | 5/1997 | Eidelberg et al. |
| 5,758,653 | A * | 6/1998 | Schotland ............... 600/407 |
| 5,807,256 | A | 9/1998 | Taguchi et al. |
| 5,813,988 | A * | 9/1998 | Alfano et al. ............. 600/476 |
| 5,905,261 | A * | 5/1999 | Schotland et al. ......... 250/341.8 |
| 5,931,789 | A * | 8/1999 | Alfano et al. ............. 600/473 |
| 5,995,857 | A | 11/1999 | Toomim et al. |
| 6,015,969 | A | 1/2000 | Nathel et al. |
| 6,088,099 | A | 7/2000 | Cabib et al. |
| 6,108,576 | A * | 8/2000 | Alfano et al. ............. 600/476 |
| 6,196,226 | B1 | 3/2001 | Hochman et al. |
| 6,205,353 | B1 * | 3/2001 | Alfano et al. ............. 600/476 |
| 6,233,480 | B1 | 5/2001 | Hochman et al. |
| 6,369,046 | B1 | 4/2002 | Schatzberg et al. |
| 6,487,428 | B1 * | 11/2002 | Culver et al. ............. 600/310 |
| 6,516,209 | B2 * | 2/2003 | Cheng et al. ............. 600/323 |
| 6,516,214 | B1 | 2/2003 | Boas |
| 6,526,309 | B1 * | 2/2003 | Chance ..................... 600/473 |
| 6,615,063 | B1 * | 9/2003 | Ntziachristos et al. ...... 600/312 |
| 6,735,458 | B2 * | 5/2004 | Cheng et al. ............. 600/323 |
| 6,956,650 | B2 * | 10/2005 | Boas et al. ................. 356/432 |
| 7,218,959 | B2 * | 5/2007 | Alfano et al. ............. 600/476 |
| 7,242,997 | B2 * | 7/2007 | Geng ........................ 700/117 |
| 7,328,059 | B2 * | 2/2008 | Sevick-Muraca et al. ... 600/473 |
| 7,398,120 | B2 | 7/2008 | Deco et al. |
| 7,565,192 | B2 * | 7/2009 | Katura et al. ............. 600/476 |
| 7,610,082 | B2 * | 10/2009 | Chance ..................... 600/475 |
| 7,860,552 | B2 * | 12/2010 | Borsook et al. ........... 600/410 |
| 7,865,230 | B1 * | 1/2011 | Sevick-Muraca et al. ... 600/473 |
| 7,904,139 | B2 * | 3/2011 | Chance ..................... 600/476 |
| 2002/0019587 | A1 * | 2/2002 | Cheng et al. ............. 600/322 |
| 2002/0035317 | A1 * | 3/2002 | Cheng et al. ............. 600/322 |
| 2002/0058867 | A1 | 5/2002 | Breiter et al. |
| 2002/0072677 | A1 * | 6/2002 | Sevick-Muraca et al. ... 600/473 |
| 2002/0099295 | A1 | 7/2002 | Gil et al. |
| 2003/0030809 | A1 * | 2/2003 | Boas et al. ................. 356/432 |
| 2003/0211121 | A1 | 11/2003 | Donovan |
| 2004/0015062 | A1 * | 1/2004 | Ntziachristos et al. ...... 600/312 |
| 2004/0030255 | A1 * | 2/2004 | Alfano et al. ............. 600/476 |
| 2004/0039267 | A1 * | 2/2004 | Kawasaki et al. .......... 600/310 |
| 2004/0087862 | A1 * | 5/2004 | Geng ........................ 600/473 |
| 2004/0092824 | A1 * | 5/2004 | Stamnes et al. ............ 600/473 |
| 2005/0055184 | A1 * | 3/2005 | Barbour et al. .............. 703/2 |
| 2005/0171434 | A1 * | 8/2005 | Madden et al. ............ 600/473 |
| 2005/0228291 | A1 * | 10/2005 | Chance ..................... 600/476 |
| 2006/0063995 | A1 * | 3/2006 | Yodh ................... A61B 5/0059 600/323 |
| 2006/0173354 | A1 * | 8/2006 | Ntziachristos et al. ...... 600/476 |
| 2006/0184043 | A1 * | 8/2006 | Tromberg et al. ........... 600/476 |
| 2006/0247531 | A1 * | 11/2006 | Pogue et al. ............... 600/476 |
| 2007/0038122 | A1 * | 2/2007 | Geng ........................ 600/476 |
| 2007/0238957 | A1 * | 10/2007 | Yared ........................ 600/407 |
| 2008/0154126 | A1 * | 6/2008 | Culver et al. ............. 600/426 |
| 2008/0262327 | A1 * | 10/2008 | Kato ................ A61B 5/14553 600/324 |
| 2009/0024021 | A1 | 1/2009 | George et al. |
| 2009/0137908 | A1 * | 5/2009 | Patwardhan ................ 600/476 |

OTHER PUBLICATIONS

Joseph et al, "Diffuse optical tomography system to image brain activation with improved spatial resolution and validation with functional magnetic resonance imaging", Applied Optics, vol. 45, No. 31, pp. 8142-8151, Nov. 1, 2006.*
Hebden et al "Optical tomography of the neonatal brain", Eur Radiol (2007) 17: 2926-2933.*
Boas et al. "Diffuse optical imaging of brain activation: approaches to optimizing image sensitivity, resolution, and accuracy" NeuroImage 23, 2004, pp. S275-S288.*
Culver, Joseph P., et al., Evidence that Cerebral Blood Volume can Provide Brain Activation Maps with Better Spatial Resolution than Deoxygenated Hemoglobin, NeuroImage, 2005, vol. 27, pp. 947-959, Elsevier, Inc., USA.
Culver, Joseph P., et al., Diffuse Optical Tomography of Cerebral Blood Flow, Oxygenation, and Metabolism in Rat During Focal Ischemia, Journal of Cerebral Blood Flow & Metabolism, The International Society for Cerebral Blood Flow and Metabolism, 2003, vol. 23, pp. 911-924, Lippincott Williams & Wilkins, Inc., Baltimore, Maryland, USA.
Colonness, Matthew T., et al., Development of Hemodynamic Responses and Functional Connectivity in Rat Somatosensory Cortex, Nature Neuroscience, 2008, vol. 11, No. 11, pp. 72-79, Nature Publishing Group, USA.
Church, Jessica A., et al., Control Networks in Paediatric Tourette Syndrome Show Immature and Anomalous Patterns of Functional Connectivity, Brain A Journal of Neurology, 2009, vol. 132, pp. 225-238, Advance Access Publication, USA.
Born, Peter, et al., Visual Activation in Infants and Young Children Studied by Functional Magnetic Resonance Imaging, Pediatric Research, International Pediatric Foundation, Inc., 1998, vol. 44(4), pp. 578-583, Lippincott Williams and Wilkins, USA.
Bonakdarpour, B., et al., Hemodynamic Response Function in Patients with Stroke-Induced Aphasia: Implications for fMRI Data Analysis, NeuroImage, 2007, vol. 36(2), pp. 322-331, National Institute of Health, Public Access Author Manuscript, USA.
Boden, S., et al., The Oxygenation Response to Functional Stimulation: Is There a Physiological Meaning to the Lag Between Parameters?, NeuroImage, 2007, vol. 36, pp. 100-107, Elsevier, Inc., USA.
Bluestone, Avraham Y., et al., Three-Dimensional Optical Tomography of Hemodynamics in the Human Head, Optics Express, 2001, vol. 9, No. 6, pp. 272-286, OSA, USA.
Biswal, Bharat F., et al., Functional Connectivity in the Motor Cortex of Resting Human Brain Using Echo-Planar MRI, MRM, 1995, vol. 34, pp. 537-541, Williams & Wilkins, USA.
Birn, Rasmus M., et al., The Effect of Respiration Variations on Independent Component Analysis Results of Resting State Functional Connectivity, Human Brain Mapping, 2008, vol. 29, pp. 740-750, Wiley-Liss, Inc., USA.
Fair, Damien A., et al., Development of Distinct Control Networks Through Segregation and Integration, Proceedings of the National Academy of Sciences, 2007, vol. 104, No. 33, pp. 13507-13512, The National Academy of Sciences, USA.
Elwell, C. E., et al., Oscillations in Cerebral Haemodynamics, Implications for Functional Activation Studies, Advances in Experimental Medicine and Biology, 1999, vol. 471, pp. 1-9, Kluwer Academic/Plenum Publishers, New York, USA.
Durduran, Turgut, et al., Diffuse Optical Measurement of Blood Flow, Blood Oxygenation, and Metabolism in a Human Brain During Sensorimotor Cortex Activation, Optics Letters, 2004, vol. 29, No. 15, pp. 1766-1768, Optical Society of America, USA.
Dunn, Andrew K., et al., Spatial Extent of Oxygen Metabolism and Hemodynamic Changes During Functional Activation of the Rat Somatosensory Cortex, NeuroImage, 2005, vol. 27, pp. 279-290, Elsevier Inc., USA.
Devor, Anna, et al., Coupling of the cortical Hemodynamic Response to Cortical and Thalamic Neuronal Activity, Proceedings of the National Academy of Sciences, 2005, vol. 102, No. 10, pp. 3822-3827, The National Academy of Sciences, USA.
Devor, Anna, et al., Coupling of Total Hemoglobin Concentration, Oxygenation, and Neural Activity in Rat Somatosensory Cortex, Neuron, 2003, vol. 39, pp. 353-359, Cell Press, USA.
D'Esposito, Mark, et al., Alternations in the Bold FMRI Signal With Ageing and Disease: A Challenge for Neuroimaging, Nature Reviews, Neuroscience, 2003, vol. 4, pp. 863-872, Nature Publishing Group, USA.
De Luca, M., et al., fMRI Resting State Networks Define Distinct Modes of Long-Distance Interactions in the Human Brain, NeuroImage, 2005, pp. 1-9, Elsevier Inc., USA.
Dehghani, Hamid, et al., Multiwavelength Three-Dimensional Near-Infrared Tomography of the Breast: Initial Simulation, Phantom, and Clinical Results, Applied Optics, 2003, vol. 42, No. 1, pp. 135-145, Optical Society of America, USA.

(56) References Cited

OTHER PUBLICATIONS

Damoiseaux, J.S., et al., Consistent Resting-State Networks Across Healthy Subjects, Proceedings of the National Academy of Sciences, 2006, vol. 103, No. 37, pp. 13848-13853, The National Academy of Sciences, USA.

Greicius, Michael D., et al., Functional Connectivity in the Resting Brain: A Network Analysis of the Default Mode Hypothesis, Proceedings of the National Academy of Sciences, 2003, vol. 100, No. 1, pp. 253-258, The National Academy of Sciences, USA.

Gibson, A. P., et al., Three-Dimensional Whole-Head Optical Tomography of Passive Motor Evoked Responses in the Neonate, NeuroImage, 2005, pp. 1-8, Elsevier, Inc., USA.

Gibson, A. P., et al., A Method for Generating Patient-Specific Finite Element Meshes for Head Modelling, Institute of Physics Publishing, Physics in Medicine and Biology, 2003, vol. 48, pp. 481-495, IOP Publishing Ltd., UK.

Fujiwara, Norio, et al., Evoked-Cerebral Blood Oxygenation Changes in False-Negative Activations in BOLD Contrast Functional MRI of Patients with Brain Tumors, NeuroImage, 2004, vol. 21, pp. 1464-1471, Elsevier, Inc., USA.

Fransson, Peter, et al., Resting-State Networks in the Infant Brain, Proceedings of the National Academy of Sciences, 2007, vol. 104, No. 39, pp. 15531-15536, The National Academy of Sciences, USA.

Franceschini, Maria Angela, et al., Diffuse Optical Imaging of the Whole Head, National Institute of Health Author Manuscript, 2006, vol. 11(5), pp. 1-22, J Biomed Opt., USA.

Fox, Michael D. and Raichle, Marcus E., Spontaneous Fluctuations in Brain Activity Observed with Functional Magnetic Resonance Imaging, Nature Reviews Neuroscience, 2007, vol. 8, pp. 700-711, Nature Publishing Group, USA.

Fox, Michael D., et al., Coherent Spontaneous Activity Accounts for Trial-to-Trial Variability in Human Evoked Brain Responses, Nature Neuroscience, 2006, vol. 9, No. 1, pp. 23-25, Nature Publishing Group, USA.

Fox, Michael D., et al., The Human Brain is Intrinsically Organized into Dynamic, Anticorrelated Functional Networks, Proceedings of the National Academy of Sciences, 2005, vol. 102, No. 27, pp. 9673-9678, The National Academy of Sciences, USA.

Fair, Damien A., et al., The Maturing Architecture of the Brain's Default Network, Proceedings of the National Academy of Sciences, 2008, vol. 105, No. 10, pp. 4028-4032, The National Academy of Sciences, USA.

Leung, Terence S., et al., Cerebral Tissue Oxygen Saturation Calculated Using Low Frequency Haemoglobin Oscillations Measured by Near Infrared Spectroscopy in Adult Ventilated Patients, Oxygen Transport to Tissue XXIX, 2008, pp. 235-244, Springer-Verlag, Berlin, Germany.

Koch, Stefan, P., et al., Synchronization Between Background Activity and Visually Evoked Potential is not Mirrored by Focal Hyperoxygenation: Implications for the Interpretation of Vascular Brain Imaging, The Journal of Neuroscience, Behavioral/Systems/Cognitive, 2006, vol. 26(18), pp. 4940-4948, Society of Neuroscience, Berlin, Germany.

Katura, Takusige, et al., Quantitative Evaluation of Interrelations Between Spontaneous Low-Frequency Oscillations in Cerebral Hemodynamics and Systemic Cardiovascular Dynamics, NeuroImage, 2006, vol. 31, pp. 1592-1600, Elsevier, Inc., USA.

Joseph, Danny K., et al., Diffuse Optical Tomography System to Image Brain Activation with Improved Spatial Resolution and Validation with Functional Magnetic Resonance Imaging, Applied Optics, 2006, vol. 45, No. 31, pp. 8142-8151, Optical Society of America, USA.

Jaskzewski, G., et al., Differences in the Hemodynamic Response to Event-Related Motor and Visual Paradigms as Measured by Near-Infrared Spectroscopy, NeuroImage, 2003, vol. 20, pp. 479-488, Academic Press, Elsevier, Inc., USA.

Iadecola, Costantino, Neurovascular Regulation in the Normal Brain and in Alzheimer's Disease, Nature Reviews Neuroscience, 2005, vol. 5, pp. 347-360, Nature Publishing Group, USA.

Heeger, David J. and Ress, David, What Does fMRI Tell us About Neuronal Activity?, Nature Reviews Neuroscience, 2002, vol. 3, pp. 142-151, MacMillian Magazines Ltd., USA.

He, Biyu J., et al, Electrophysiological Correlates of the Brian's Intrinsic Large-Scale Functional Architecture, Proceedings of the National Academy of Sciences, 2008, vol. 105, No. 41, pp. 16039-16044, The National Academy of Sciences, USA.

Greicius, MD; MPH; Michael D., et al., Resting-State Functional Connectivity in Major Depression: Abnormally Increased Contributions from Subgenual Cingulate Cortex and Thalamus, National Institute of Health, 2007, vol. 62(5), pp. 429-437, NIH Public Access, Author Manuscript, USA.

Greicius, Michael D., et al., Default-Mode Network Activity Distinguishes Alzheimer's Disease from Healthy Aging: Evidence from functional MRI, Proceedings from the National Academy of Sciences, 2004, vol. 101, No. 13, pp. 4637-4642, The National Academy of Sciences, USA.

Schroeter, Matthias L., et al., Spontaneous Slow Hemodynamic Oscillations are Impaired in Cerebral Microangiopathy, Journal of Cerebral Blood Flow & Metabolism, 2005, vol. 25, pp. 1675-1684, ISCBFM, jcbfm.com.

Saager, Rolf B., and Berger, Andrew J., Direct Characterization and Removal of Interfering Absorption Trends in Two-Layer Turbid Media, Journal of the Optical Society of America, 2005, vol. 22, No. 9, pp. 1874-1882, Optical Society of America, USA.

Rowley, A. B., et al., Synchronization Between Arterial Blood Pressure and Cerebral Oxyhaemoglobin Concentration Investigated by Wavelet Cross-Correlation, Institute of Physics Publishing, Physiological Measurement, 2007, vol. 28, pp. 161-173, IOP Publishing Ltd, UK.

Roche-Labarbe, N., et al., Coupled Oxygenation Oscillation Measured by NIRS and Intermittent Cerebral Activation on EEG in Premature Infants, NeuroImage, 2007, vol. 36, pp. 718-727, Elsevier, Inc., USA.

Reinhard, Matthias, et al., Oscillatory Cerebral Hemodynamics—the Macro- vs. Microvascular Level, Journal of the Neurological Sciences, 2006, vol. 250, pp. 103-109, Elsevier, Inc., USA.

Raichle, Marcus E. and Mintun, Mark A., Brain Work and Brain Imaging, Annual Review of Neuroscience, 2006, vol. 29, pp. 449-476, Annual Reviews, USA.

Obrig, Hellmuth and Villringer, Arno, Beyond the Visible-Imaging the Human Brain with Light, Journal of Cerebral Blood Flow & Metabolism, The International Society for Cerebral Blood Flow and Metabolism, 2003, vol. 23, pp. 1-18, Lippincott Williams & Wilkinss, Inc., Philadelphia, USA.

Obrig, Hellmuth, et al., Spontaneous Low Frequency Oscillations of Cerebral Hemodynamics and Metabolism in Human Adults, NeuroImage, 2000, vol. 12, pp. 623-639, Academic Press, USA.

Morita, Tomoyo, et al., Difference in the Metabolic Response to Photic Stimulation of the Lateral Geniculate Nucleus and the Primary Visual Cortex of Infants: a fMRI Study, Neuroscience Research, 2000, vol. 38, pp. 63-70, Elsevier Science Ireland Ltd, and the Japan Neuroscience Society.

Lowe, M. J., et al., Functional Connectivity in Single and Multislice Echoplanar Imaging Using Resting-State Fluctuations, NeuroImage, 1998, vol. 7, Article No. N1970315, pp. 119-132, Academic Press, USA.

Zou, Ping, et al., Bold Responses to Visual Stimulation in Survivors of Childhood Cancer, NeuroImage, 2005, vol. 24, pp. 61-69, Elsevier, Inc., USA.

Zhang, Dongyan, et al., Intrinsic Functional Relations Between Human Cerebral Cortex and Thalamus, Journal of Neurophysiology, 2008, vol. 100, pp. 1740-1748, The American Physiological Society, USA.

Zeff, Benjamin W., et al, Retinotopic Mapping of Adult Human Visual Cortex with High-Density Diffuse Optical Tomography, Proceedings of the National Academy of Sciences, 2007, vol. 104, No. 29, p. 12169-12174, The National Academy of Sciences, USA.

Yodh, Arjun and Chance, Britton, Spectroscopy and Imaging with Diffusing Light, Physics Today, 1995, pp. 34-40, American Institute of Physics, USA.

Van Essen, PhD, David C., et al, An Integrated Software Suite for Surface-Based Analyses of Cerebral Cortex, Journal of the Ameri-

(56) References Cited

OTHER PUBLICATIONS can Medical Informatics Association, 2001, vol. 8, No. 5, pp. 443-459, Journal of the American Medical Informatics Association, USA.

Tachtsidis, Ilias, et al., Investigation of Cerebral Haemodynamics by Near-Infrared Spectroscopy in Young Healthy Volunteers Reveals Posture-Dependent Spontaneous Oscillations, Institute of Physics Publishing, Physiological Measurement, 2004, vol. 25, pp. 437-445, IOP Publishing Ltd., UK.

Steinbrink, Jens, et al., Illuminating the BOLD Signal: Combined fMRI-fNIRS Studies, Magnetic Resonance Imaging, 2006, vol. 24, pp. 495-505, Elsevier, Inc., USA.

Shmueli, Karin, et al., Low-Frequency Fluctuations in the Cardiac Rate as a Source of Variance in the Resting-State fMRI Bold Signal, NeuroImage, 2007, vol. 38, pp. 306-320, Elsevier, Inc., USA.

Sheth, Sameer A., et al., Columnar Specificity of Microvascular Oxygenation and vol. Responses: Implications for Functional Brain Mapping, The Journal of Neuroscience, 2004, vol. 24(3), pp. 634-641, Society for Neuroscience, USA.

Notification of Transmittal of the International Search Report and the Written Opinion of the International Searching Authority, or Declaration, Date of Mailing, May 1, 2009, International Application No. PCT/US2007/088601, p. 18.

McKeown, Martin J. et al., Independent component analysis of functional MRI: what is signal and what is noise?, Current Opinion in Neurobiology, vol. 13, Oct. 2003, pp. 620-629.

Culver, J. et al., "Diffuse Optical Tomography for Mapping Human Brain Function," Life Science Systems and Applications Workshop, 2006 (Jul. 1, 2006), pp. 1-8.

Culver, J. et al., "Volumetric Diffuse Optical Tomography of Brain Activity," Nov. 1, 2003, vol. 28, No. 21, pp. 2061-2063, Optics Letters.

Fox, Michael D. et al., The Human Brain is Intrinsically Organized into Dynamic Anticorrelated Functional Networks, Proceedings of the National Academy of Sciences of the United States of America 2005; vol. 102, pp. 9673-9678.

Hyvarinen A. Fast and Robust Fixed-Point Algorithms for Independent Component Analysis, IEEE Transactions on Neural Networks, 1999; vol. 10, pp. 626-634.

Hyvarinen A. and Oja, E., "Independent Component Analysis: Algorithms and Applications", Neural Networks 2000; vol. 13, pp. 411-430.

Onton J. et al., "Imaging Human EEG Dynamics Using Independent Component Analysis", Neuroscience and Biobehavorial Reviews 2006; vol. 30, pp. 808-822.

Mantini D. et al., "Complete Artifact Removal for EEG Recorded During Continuous Fmri Using Independent Component Analysis", Neuroimage 2007; vol. 34, pp. 598-607.

* cited by examiner

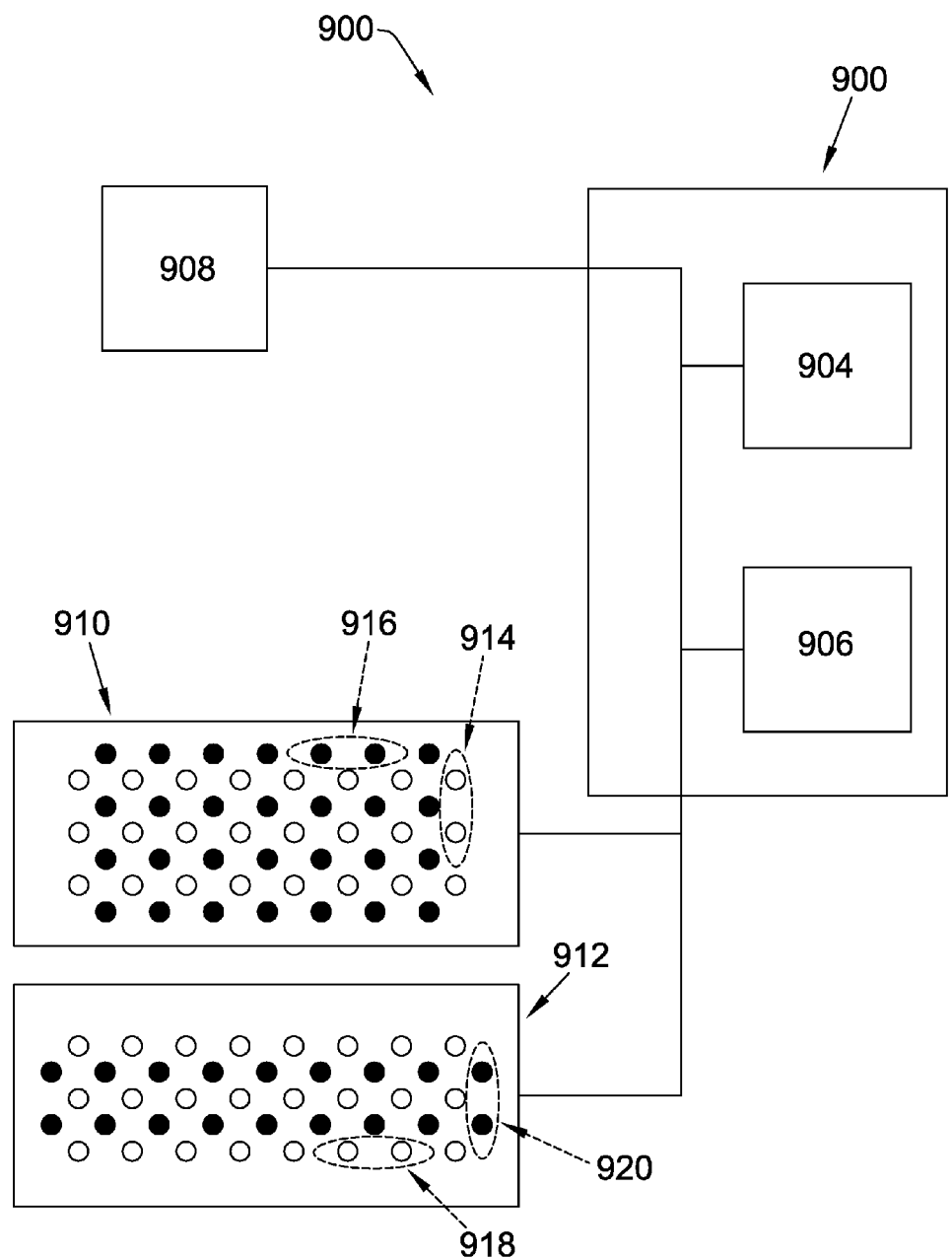

TASK-LESS OPTICAL MAPPING OF DYNAMIC BRAIN FUNCTION USING RESTING STATE FUNCTIONAL CONNECTIVITY

CROSS REFERENCE TO RELATED APPLICATION

This application claims the benefit of U.S. Provisional Patent Application No. 61/045,855 filed Apr. 17, 2008, which is hereby incorporated by reference in its entirety.

STATEMENT REGARDING FEDERALLY SPONSORED RESEARCH & DEVELOPMENT

This invention was made with government support under grants R21 EB00792401 and K25 NS44339 awarded by the NIH. The government has certain rights in the invention.

BACKGROUND

The embodiments described herein relate generally to optical imaging and, more particularly, to diffuse optical imaging (DOI) using either traditional near infrared spectroscopy (NIRS) systems or more advanced diffuse optical tomography (DOT) systems.

Optical neuroimaging has never lacked clinical potential, due to its ability to longitudinally and non-invasively monitor brain function. However, progress towards the bedside practice of methods to map brain function, such as functional near infrared spectroscopy (fNIRS), has been hindered by conceptual and technical limitations. One obstacle is that task-based neuroimaging, which is standard in cognitive neuroscience research, is generally ill-suited to clinical populations since they may be unable to perform any task. Recently in functional magnetic resonance imaging (fMRI), it was discovered that even during the absence of overt tasks, fluctuations in brain activity are correlated across functionally-related cortical regions. Thus, the spatial and temporal evaluation of spontaneous neuronal activity has allowed mapping of these resting-state networks (RSNs). Translating these advances to optical techniques would enable new clinical and developmental studies. Yet, mapping spontaneous activity with fNIRS measurements presents significant challenges due to the obscuring influences of superficial signals, systemic physiology, and autoregulation.

Accordingly, it is desirable to provide a method for using optical imaging to image functional connectivity patterns in the human brain.

SUMMARY

Embodiments of the invention provide systems and methods for method for utilizing an optical system to map brain function. An exemplary method includes determining a time series of light measurements for a plurality of spatially distributed source and detector pairs, receiving the light measurements over a period of time using the source-detector pairs, and producing at least one map of a respective strength of each of a plurality of temporal correlations. The temporal correlations are based on the time series of the spatially distributed source and detector pairs and the received light measurements.

BRIEF DESCRIPTION OF THE DRAWINGS

Aspects of the invention may be better understood by referring to the following descriptions in conjunction with the accompanying drawings.

FIG. 9 is a block schematic diagram of an exemplary optical imaging system.

Corresponding reference characters indicate corresponding parts throughout the drawings.

DETAILED DESCRIPTION

Figure 1A:
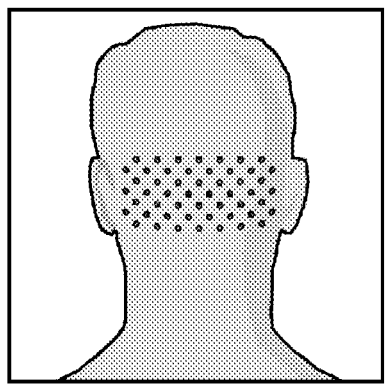
FIGS. 1A and 1B are schematic diagrams of a visual cortex imaging pad and a motor cortex imaging pad, respectively.

Embodiments of the invention will work with any optical imaging system that provides a temporal series of functional images of the brain. One example of an optical imaging system that is operable with embodiments of the invention is described in a co-pending U.S. patent application Ser. No. 11/962,513 filed Dec. 21, 2007, entitled "HIGH PERFORMANCE IMAGING SYSTEM FOR DIFFUSE OPTICAL TOMOGRPAHY AND ASSOCIATED METHOD OF USE," the entirety of which is hereby incorporated by reference herein for all purposes.

Embodiments of the invention provide systems and methods for using diffuse optical tomography (DOT) to image functional connectivity patterns in the human brain. Optical imaging systems may include high density DOT systems or any other suitable system operable to measure and analyze brain function using optical contrasts to provide maps of resting-state functional connectivity patterns.

Low frequency fluctuations in cerebral hemodynamics have been detected by NIRS. However, as the optical signal is a mixture of hemodynamics within the scalp, skull, and brain, it is particularly susceptible to artifacts from systemic changes. Such fluctuations have been found to obscure functional responses in fNIRS studies. In addition, their frequency components overlap those of RSNs. As with fc-MRI, these systemic contributions must be removed to observe the underlying spatial maps of the brain networks. In part because fNIRS has traditionally had difficulty in separating different physiologic contributions, previous resting-state studies have focused on investigating the correlation between the measured signal and systemic physiological variables. While such experiments have yielded interesting results, they have not moved beyond temporal analysis to the study of spatial correlations and neural connectivity. In addition, fNIRS also suffers from spatial limitations. Low spatial resolution (>3 cm) may average out any underlying spatial correlation structure. In addition, an fNIRS study to detect RSNs requires a field-of-view greater than typically available in order to cover both correlated and uncorrelated (e.g., control) brain regions.

While there are multiple challenges, both physiological and methodological, to the development of fc-DOI (e.g., fc-NIRS or fc-DOT) systems, their successful creation would open up new approaches to the research of resting-state physiology. The discovery of functional connectivity (fc-MRI) has led to its use as an important tool throughout neuroimaging research, including insights into childhood brain development. Recent fc-MRI studies have found RSNs that are altered in patients with depression, Alzheimer's disease, and Tourette's syndrome. However, important brain injured populations, such as intensive care patients, cannot be easily transported to fixed scanner environments. The portability and wearability of fc-DOI systems could allow significant applications in populations that are not amenable to traditional functional neuroimaging, such as hospitalized patients and young children.

In addition, DOT provides a more comprehensive assessment of hemodynamics and metabolism than the blood oxygenation level-dependent (BOLD) signal, due to BOLD's complicated connection to the underlying neurovascular coupling. While relying on the neurovascular response in much the same manner as BOLD-fMRI, DOT can measure changes in oxyhemoglobin ($HbO_2$), deoxyhemoglobin (HbR), and total hemoglobin (HbT) (the BOLD contrast is mostly sensitive to HbR) at a much higher sampling rate (at least 10 Hz, compared to ~0.5 Hz with fMRI). This enhanced view of brain activity is especially important when the neurovascular coupling is either unknown (as in infants) or altered (as with brain injury).

Accordingly, embodiments of the invention provide fc-DOI that provides imaging of distributed cortical regions. These spatial imaging techniques are complemented by linear regression methods that remove global superficial signals and correlation analyses to map spontaneous brain activity patterns.

The success of fc-DOT is evaluated by an ability to obtain spatial correlations maps based on local physiology that match the fc-MRI literature and subject-matched fc-MRI experiments. Functional connectivity was first demonstrated by BOLD-fMRI detecting low-frequency variations in the motor cortex during the resting state. The original validation for fc-MRI was that the resulting spatial correlations corresponded with the brain's functional architecture as mapped by task-induced responses. Previous fc-MRI studies have also demonstrated that the motor and visual cortices constitute largely independent functional networks, each exhibiting high levels of inter-hemispheric correlation. Thus, it had been expected that resting-state analysis of seed regions found from a sensory task-response study would reveal that sensory network, while the other sensory network will provide a control that should be uncorrelated. These exemplary studies aim to establish the utility of DOT for functional connectivity analysis.

During a study, healthy adult subjects were recruited (1 male, 4 female, ages 24-27). For DOT imaging, subjects were seated in an adjustable chair facing a 19-inch LCD screen at an approximately 70.0 centimeter (cm) viewing difference. DOT imaging arrays were placed over the occipital and sensorimotor cortices and held in place with hook-and-look strapping. The position of the pads was measured to establish repeatable positioning.

Figure 1B:
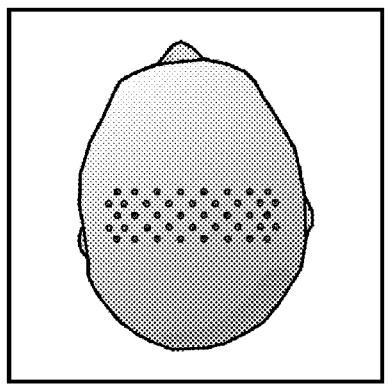
Figure 1C:
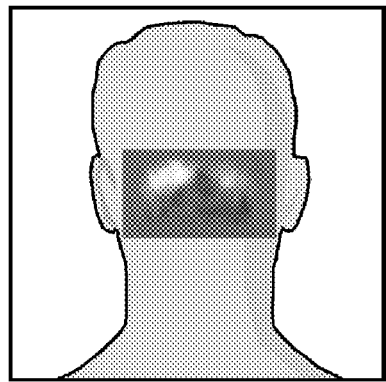
FIGS. 1C and 1D are images illustrating cortex activations shown placed over the occipital cortex and the sensorimotor cortex, respectively.
Figure 1D:
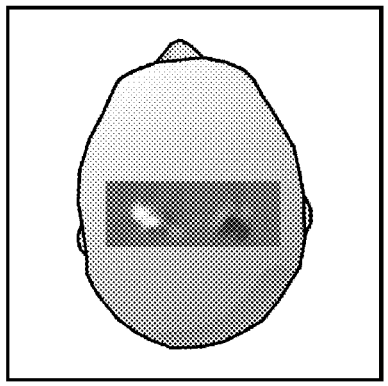

FIG. 1A is an exemplary schematic of the visual cortex imaging pad, with 24 sources and 28 detectors. FIG. 1B is an exemplary schematic of the motor cortex imaging pad, with 24 sources and 18 detectors. FIG. 1C is a left visual cortex activation ($\Delta HbO_2$) placed over the occipital cortex to show direction-of-view. All visual cortex images are posterior coronal projections of a cortical shell. FIG. 1D is a motor cortex activation ($\Delta HbO_2$) placed over the sensorimotor cortex to show direction-of-view. All motor cortex images are superior axial projections of a cortical shell.

Embodiments of the DOT system described herein include fiber optic arrays arranged in high-density grids: one over the visual cortex (24 sources×28 detectors, overall dimensions 14×6.5 cm) and one over the motor cortex (24 sources×18 detectors, overall dimensions 16×4.5 cm) as shown in FIGS. 1A and 1B. The fiber optics couple the subject's head to sources and detectors. Every source position includes LEDs at two near-infrared wavelengths (750 and 850 nm); each independently modulated with high-bandwidth (20 MHz) digital I/O lines. Detectors were avalanche photodiodes with dedicated 24-bit analog-to-digital converters. Data was saved direct to disk at 96 kHz.

Activation studies were performed to locate the motor and visual cortices. The visual cortex was defined using reversing checkerboard grids (10 Hz reversal on 50% gray background, 10 sec on and 20 sec off). The right and left sensorimotor cortices were similarly defined with pseudo-random blocks of right and left finger tapping (3 Hz tapping, 10 sec on and 20 sec off). For resting-state analysis, a 50% gray screen with a crosshair was viewed (three 5 min blocks for 15 min total).

Activation data were converted to log-ratio and high-pass filtered (0.02 Hz) to remove long-term drift. An average of all first-nearest-neighbor measurements on each pad was constructed as an estimate of global and superficial signals. This signal was then regressed from all measurements within each pad. After a low-pass filter (0.5 Hz) removed residual pulse signals, the time traces were used for image reconstruction. Resting-state data underwent similar steps (including an identical linear regression of superficial signals), except the initial high-pass filter was 0.009 in order to preserve low-frequency connectivity signals. After each 5 minute block of resting-state data was preprocessed, the results were concatenated to a 15 minute time series.

A two-layer head model was used with finite-element software (NIRFAST) to generate a forward light-sensitivity matrix of the DOT array. Prior to inversion, channels with high standard deviation were considered corrupted by motion artifact and were removed from the reconstruction for a given run. The inverted sensitivity matrix converts time series measurement data into three-dimensional a series of differential absorption images for each wavelength. Concentrations of oxyhemoglobin and deoxyhemoglobin were then obtained using their extinction coefficients at the two wavelengths. Total hemoglobin was then obtained as a simple sum of the two hemoglobin species. From this series of three-dimensional images, a cortical shell was selected and all images are shown as projections of this shell. For example, FIGS. 1C and 1D are projections from the posterior coronal view for images of the visual cortex and from the superior horizontal view for the motor cortex, respectively.

Activation images were obtained by block-averaging each subject's trials and temporally averaging (5 seconds) around the peak hemodynamic response. For each of the four stimuli (left/right visual and left/right motor) and for each subject, a 1 $cm^3$ volume was chosen as a seed region for correlation analysis. Resting-state images were low-pass filtered (0.08 Hz). The resting-state time traces from each seed region were then averaged to create a seed signal, which was then correlated with every other pixel in the field-of-view of both imaging pads.

DOT imaging was performed simultaneously with high-density grids placed over the visual and motor cortices, as shown in FIGS. 1A and 1B. Seed regions for later functional connectivity analysis were determined with activation paradigms (right/left flickering checkerboards for visual cortex and right/left finger-tapping for motor cortex). The imaging procedure yields maps of differential changes in the concentrations of oxyhemoglobin, deoxyhemoglobin, and total hemoglobin. As shown in FIGS. 1C and 1D, all four stimuli generated activations with high contrast-to-noise, with the shape of the activation consistent across the three contrasts. From these activation images, seeds regions (1 cm$^3$) were chosen for use in the correlation analysis.

Figure 2A:
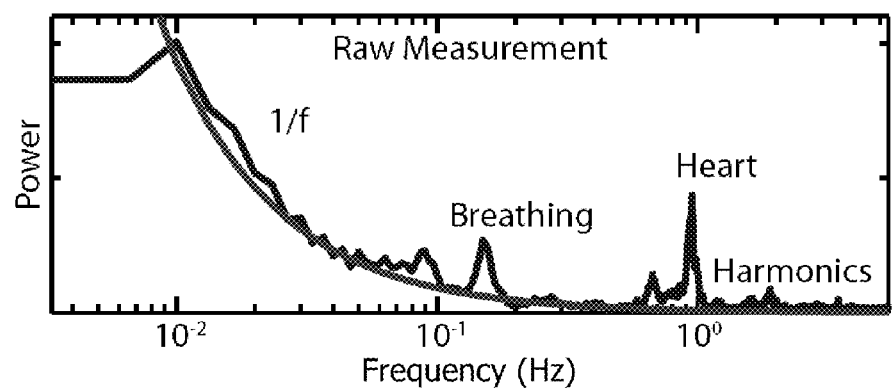
FIGS. 2A, 2B, and 2C are diagrams illustrating exemplary power spectra of resting-state optical measurements.
Figure 2B:
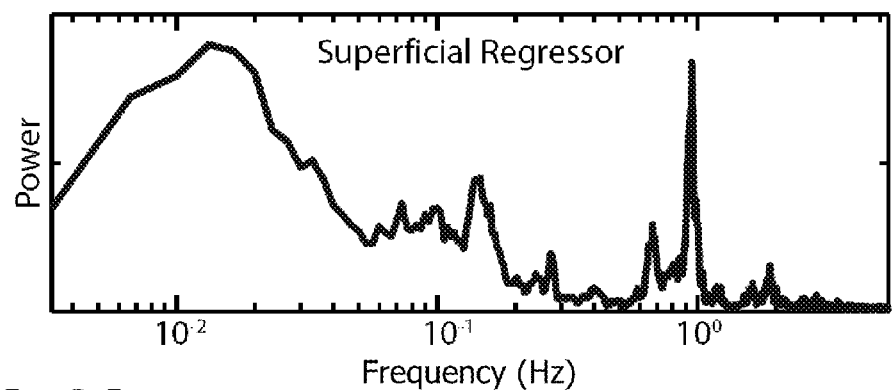
Figure 2C:
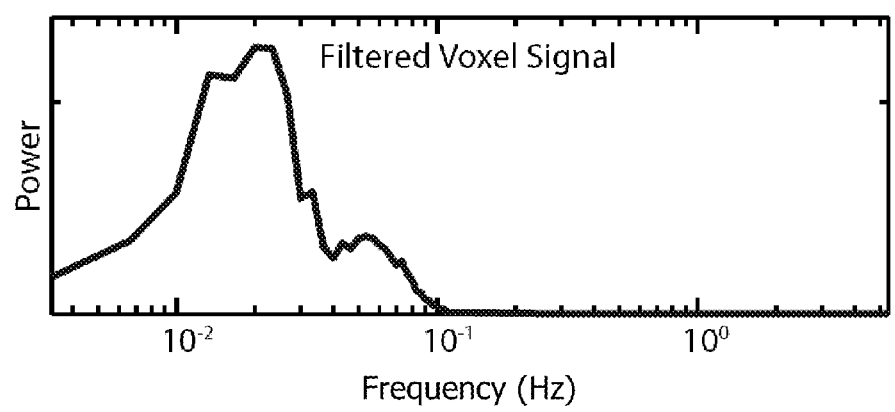

FIGS. 2A, 2B, and 2C illustrate exemplary power spectra of resting-state optical measurements ($\Delta HbO_2$). Specifically, FIG. 2A illustrates a spectral power of a single second-nearest neighbor resting-state time trace, sampling both brain and superficial tissues, before the application of any filters. The low frequency components follow a 1/f curve, and there are peaks at the respiratory (0.16 Hz) and cardiac (0.95 Hz) rates. FIG. 2B illustrates a spectral power of the superficial regressor derived from all the first-nearest neighbor measurements. These systemic low frequency fluctuations are removed from the data prior to performing functional connectivity mapping. FIG. 2C illustrates a spectral power of a filtered, imaged signal from a single voxel. This remaining spectral power within the desired frequency range is used to perform functional connectivity mapping.

As shown in FIG. 2A, a spectral analysis of resting-state measurements (5 minutes) showed 1/f components as well as distinct peaks attributable to cardiac (0.75-1 Hz) and respiratory (0.1-0.3 Hz) frequencies. Since the temporal sampling rate of the DOT system (10.8 Hz) is much higher than that of typical fMRI (~0.5 Hz), these physiologic confounds were not aliased into lower frequency bands. However, there are also vascular confounds from systemic auto-regulation that occur within the same frequency range as resting-state network correlations. Moreover, as shown in FIG. 2B, using a subset of signals that have minimal penetration into the brain facilitates construction of measures of each pad's scalp hemodynamics. Every channel had the superficial/global signal removed by regression and was band-pass filtered. Three-dimensional image reconstructions of these source-detector measurements then allowed the localization of brain physiology. As shown in FIG. 2C, this processing was designed to result in voxel time courses that are unobscured by systemic confounds.

Figures 3A, 3B, 3C, 3D, 3E, 3F, 3G, 3H, 3I, 3J, 3K, 3L:
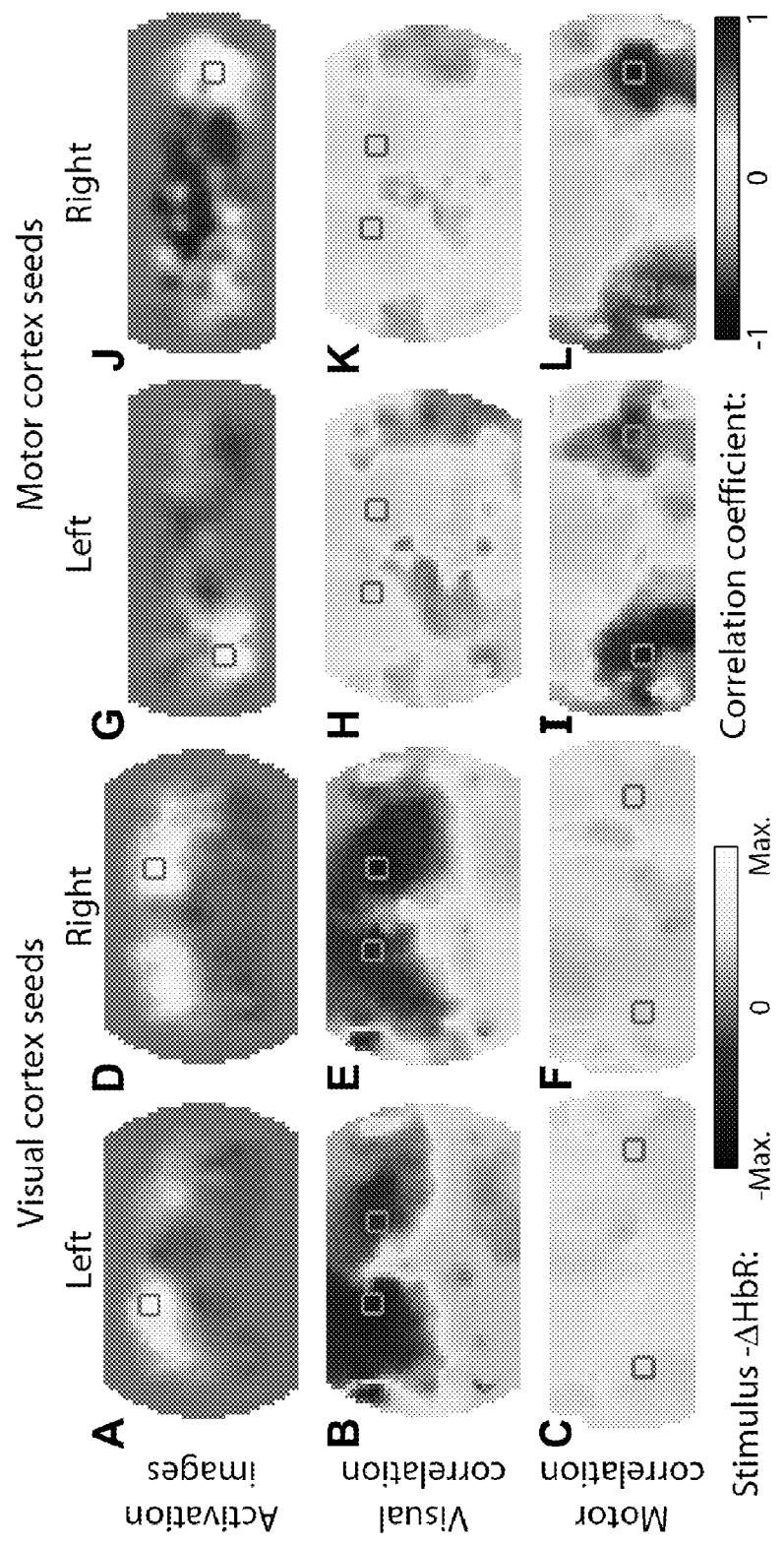
FIGS. 3A through 3L are images illustrating exemplary functional connectivity mapping for a single subject.

FIGS. 3A through 3L illustrate exemplary functional connectivity mapping ($\Delta HbR$, Subject 1, Session 1). Specifically, FIG. 3A illustrates an activation in the left visual cortex due to a right visual stimulus. There is a decrease in the concentration of deoxyhemoglobin with high contrast-to-noise. The left visual cortex seed is defined by the gray box. FIG. 3B shows a correlation map in the visual cortex using the left visual cortex seed. There is correlation with both hemispheres of the visual cortex, but not with the lower region of the pad. Both right and left seed boxes are shown. FIG. 3C shows a correlation map in the motor cortex using the left visual cortex seed. There is only low correlation throughout the field-of-view. Both right and left motor seed boxes as defined in FIGS. 3A through 3L are shown for reference. FIGS. 3D through 3F illustrate an analysis performed using the right visual cortex seed. Note the similar pattern. FIGS. 3G through 3L illustrate an analysis performed using motor cortex seeds. Note the inter-hemispheric correlations in the motor cortex with only low correlations to the visual cortex.

The time traces for oxyhemoglobin, deoxyhemoglobin, and total hemoglobin for these seed regions were then analyzed over 15 minutes of resting-state brain activity. For each seed time course, the correlation coefficient with each cortical voxel's time course is determined. As shown in FIGS. 3A through 3F, for the visual seeds, the images show that each seed region is correlated with the surrounding cortex, the more lateral cortex, and the contralateral cortex. In addition, there is no correlation with the visual seeds throughout the motor cortex, which has a flat correlation profile. Similarly, correlation maps for the motor cortex seeds result in symmetrical correlation with the contralateral motor cortex, but not with the visual cortex, which is shown in FIGS. 3G through 3L.

Referring to FIGS. 4A through 4F, correlation analysis performed on the same subject over multiple days demonstrated the method's robustness. Correlation maps were found for all 3 subjects. FIGS. 5A through 5F show that the patterns are similar between all subjects. Moreover, the average maps over all subjects, as shown in FIGS. 6A through 6H showed the same pattern as in FIGS. 3A through 3L.

Figures 4A, 4B, 4C, 4D, 4E, 4F:
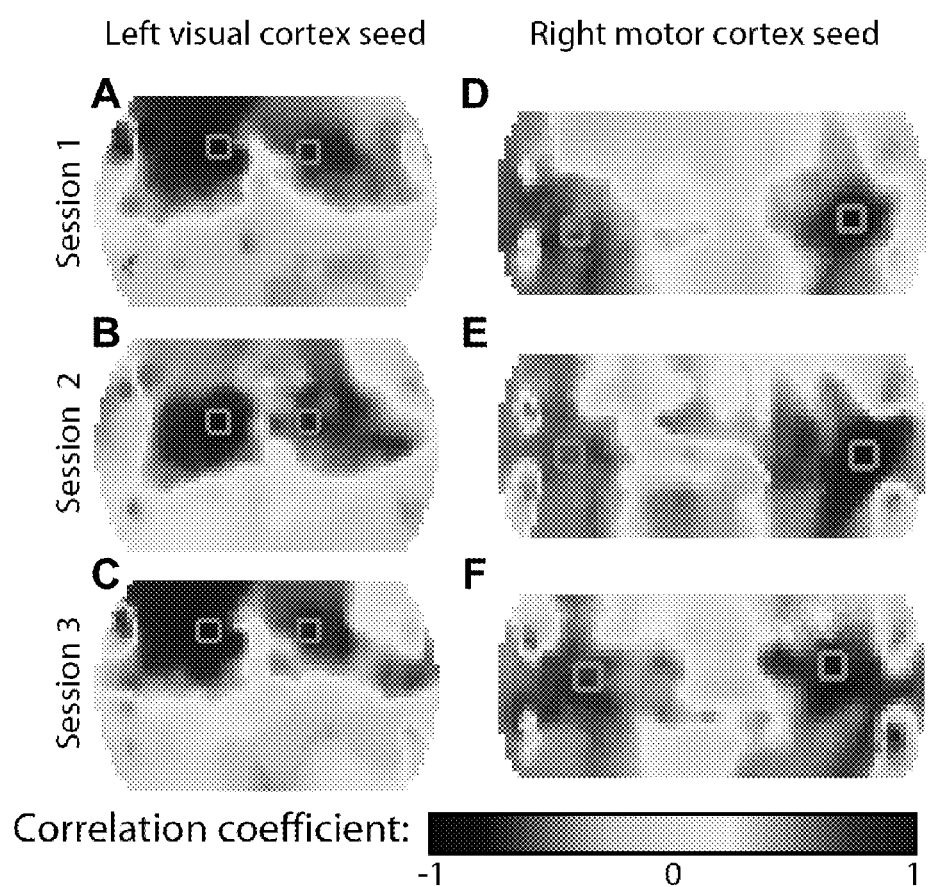
FIGS. 4A through 4F are images illustrating exemplary functional connectivity over multiple days for a single subject.

FIGS. 4A through 4F illustrate exemplary functional connectivity over multiple days in the same subject ($\Delta HbR$, subject 1). Specifically, FIGS. 4A through 4C are correlation maps within the visual cortex from the left visual cortex seed, and FIGS. 4D through 4F are correlation maps within the motor cortex from the right motor cortex seed.

Correlation analysis was performed for all three hemoglobin contrasts. As shown in FIGS. 4A, 4B, and 4C, all three contrasts show inter-hemispheric correlations. FIG. 4D shows that statistical analysis across all subjects and contrasts confirms that correlations within the motor and visual networks are significantly above the baseline correlations.

Figures 5A, 5B, 5C, 5D, 5E, 5F:
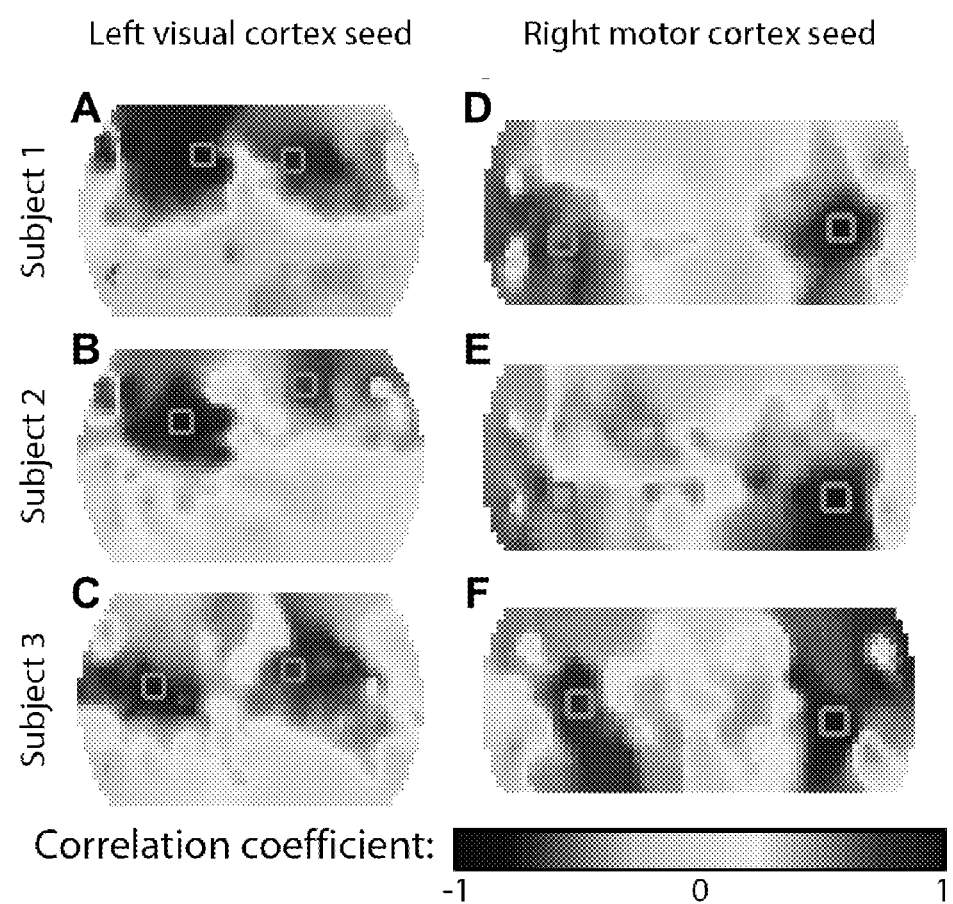
FIGS. 5A through 5F are images illustrating exemplary functional connectivity for multiple subjects.

FIGS. 5A through 5F illustrate exemplary functional connectivity in multiple subjects ($\Delta HbR$). Specifically, FIGS. 5A, 5B, and 5C are correlation maps within the visual cortex from the left visual cortex seed, and FIGS. 5D, 5E, and 5F are correlation maps within the motor cortex from the right motor cortex seed.

Figures 6A, 6B, 6C, 6D, 6E, 6F, 6G, 6H:
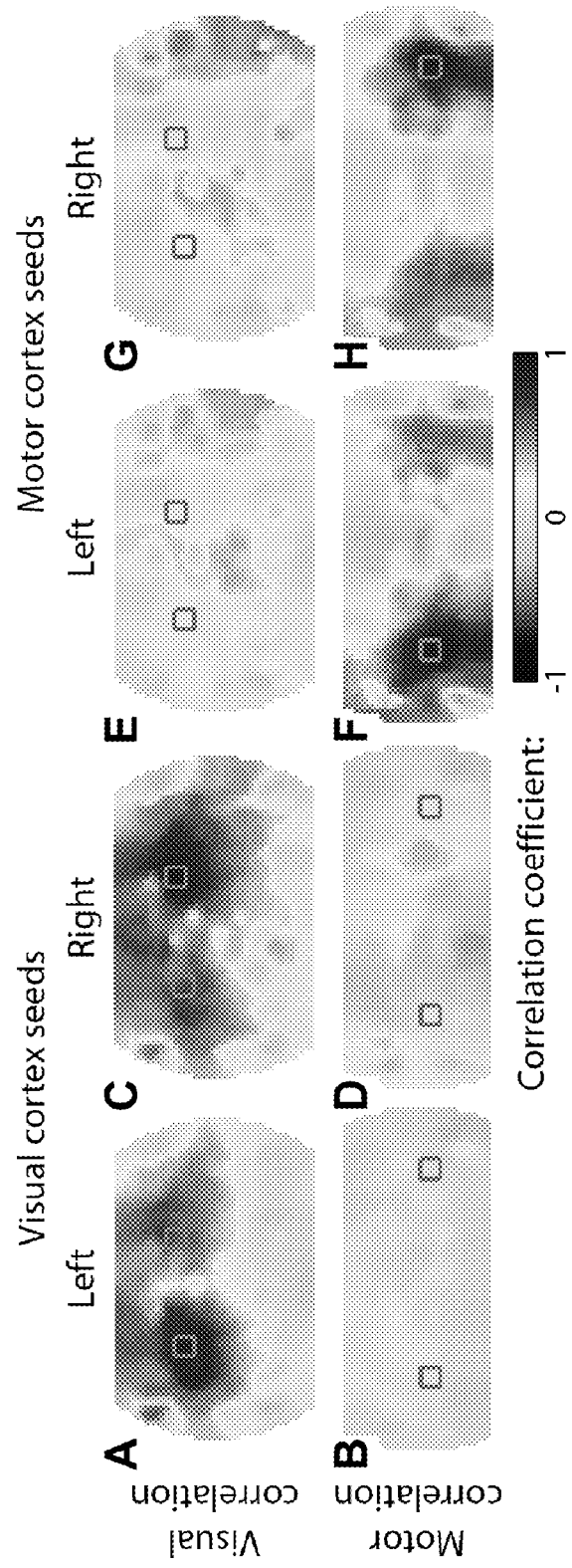
FIGS. 6A through 6H are images illustrating exemplary functional connectivity using average data values for multiple subjects.

FIGS. 6A through 6H illustrate exemplary functional connectivity using the average over multiple subjects ($\Delta HbR$). Specifically, FIG. 6A is a correlation map in the visual cortex from the left visual cortex seed. There is correlation with both hemispheres of the visual cortex, but not with the lower region of the pad. FIG. 6B is a correlation map in the motor cortex using the left visual cortex seed. The correlation throughout the field-of-view is low. FIGS. 6C through 6H are correlation maps using the other seed regions.

Figures 7A, 7B, 7C, 7D:
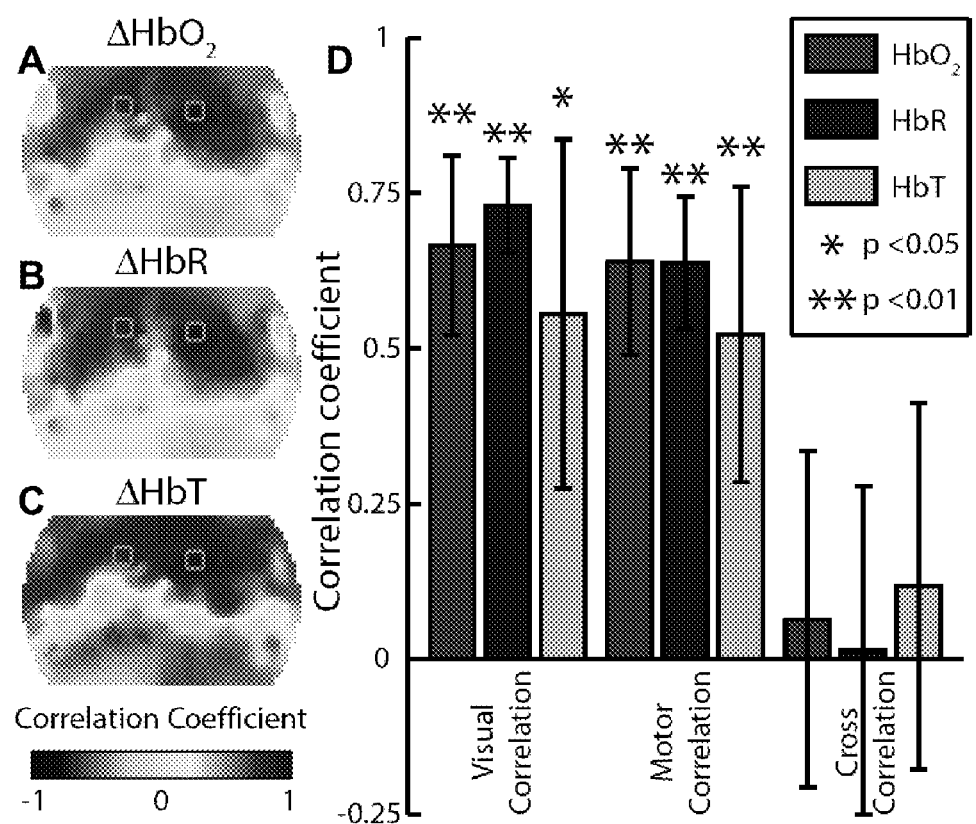
FIGS. 7A through 7D are images illustrating an exemplary analysis of functional connectivity for multiple contrasts.

FIGS. 7A through 7D illustrate an exemplary analysis of functional connectivity for all three contrasts ($HbO_2$, HbR, and HbT). Specifically, FIGS. 7A, 7B, and 7C are visual correlation maps using the right visual cortex seed for each of the three contrasts (Subject 1, Session 1). FIG. 7D is a graph of correlation coefficients across multiple subjects and days for all three contrasts (mean and standard deviation). The p-value comparing each inter-hemispheric correlation to the visual-to-motor correlation within each contrast is shown. Visual and motor networks are significantly correlated with all three contrasts, while there is little correlation between the visual and motor cortices.

Figures 8A, 8B, 8C, 8D:
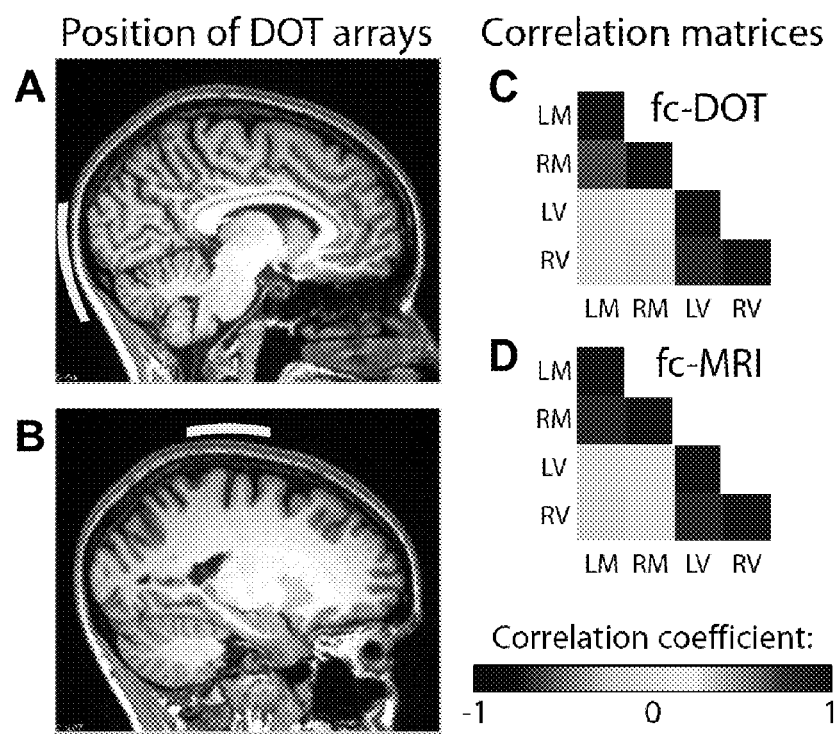
FIGS. 8A through 8L are images illustrating an exemplary demonstration of a similarity between maps acquired using fc-MRI and maps acquired using DOT.
Figures 8E, 8F, 8G, 8H:
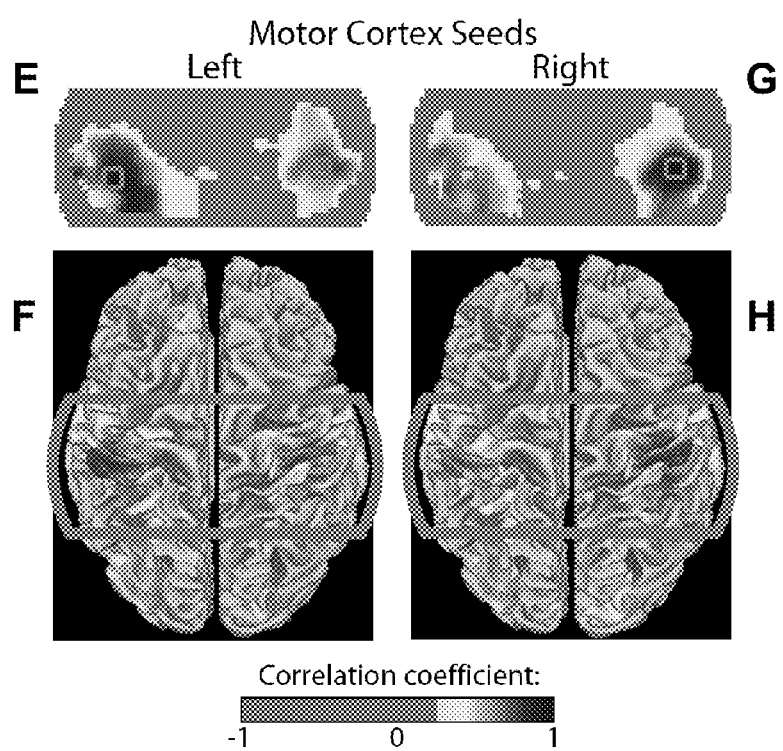
Figures 8I, 8J, 8K, 8L:
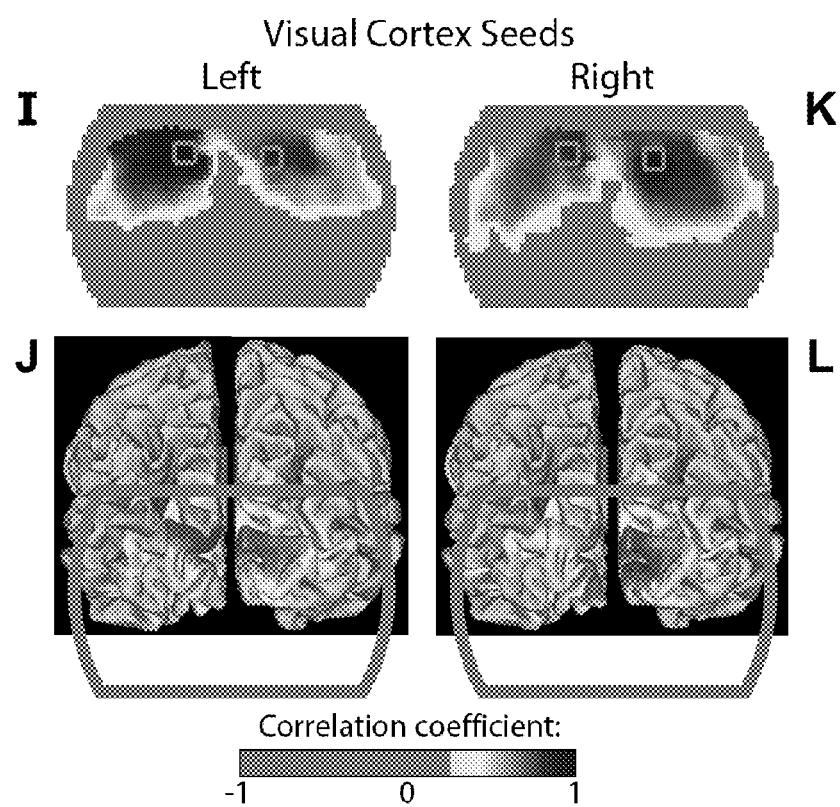

Subject-matched fc-MRI experiments confirmed that networks mapped with optical techniques match those found with MRI. FIGS. 8A through 8L illustrate an exemplary demonstration of the similarity of maps from fc-MRI and those from other optical techniques (subject 1). Specifically, FIG. 8A is an image of a sagittal slice (5 mm left of midline) from the subject's anatomical MRI with schematic of the visual cortex pad superimposed, showing its position over the visual cortex. FIG. 8B is an image of a sagittal slice (18 left of midline) from an anatomical MRI with schematic of the motor cortex pad superimposed, showing its position over the central sulcus. FIG. 8C is a cross-correlation matrix of all four seeds from the optical imaging. Note the high inter-hemispheric correlations and low correlations between the motor and visual networks. FIG. 8D is a cross-correlation matrix for all four seeds from fc-MRI imaging. Note the similarity to the optical correlation matrix. FIG. 8E is an image of an optical correlation map using the left motor cortex seed. FIG. 8F is an fc-MRI correlation map, dorsal view, using the left motor cortex seed. The optical motor cortex imaging pad's location is shown in cyan. FIGS. 8G through 8L are optical and fc-MRI correlation maps using the other seed locations highlighting their similar patterns.

FIG. 9 is a block schematic diagram of an exemplary optical imaging system 900 that may be used to map brain function as described in detail above. In the exemplary embodiment, system 900 includes a computer 902 that includes a processor 904 and a memory 906 coupled to processor 904. Moreover, system 900 includes a display 908, such as an LCD screen, a visual cortex imaging pad 910, and a motor cortex imaging pad 912, which are each coupled, such as communicatively coupled, to computer 902. Display 908 and imaging pads 910 and 912 may be coupled to computer 902 via a network, communication cables, and/or any other suitable communication means. As described in detail above, each imaging pad 910 and 912 is positioned with respect to a subject's occipital and sensorimotor cortices, respectively. Specifically, as described above, visual cortex imaging pad 910 includes a fiber optic array that is arranged in a grid of twenty-four sources 914 and twenty-eight detectors 916. Motor cortex imaging pad 912 similarly includes a fiber optic array that is arranged in a grid of twenty-four sources 918 and eighteen detectors 920. In the exemplary embodiment, each element of system 900 is adapted to perform the steps described above to facilitate mapping brain function.

Figure 10:
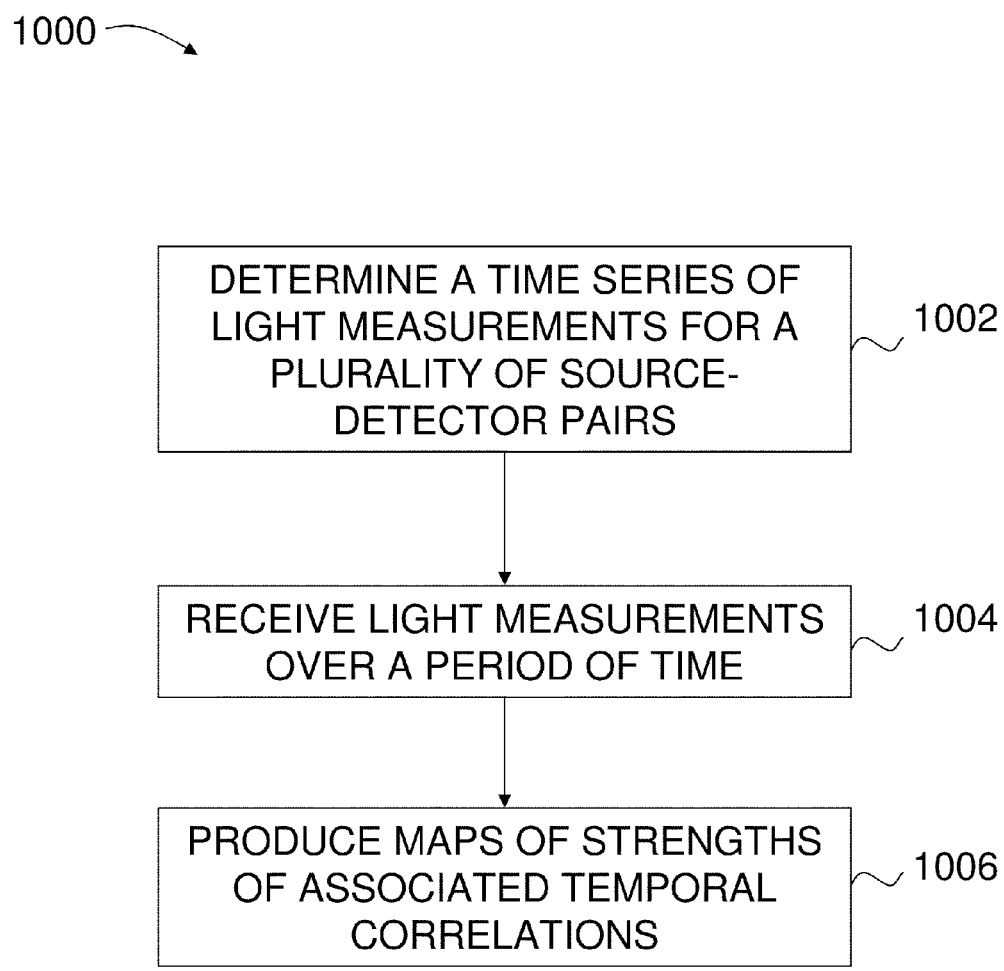
FIG. 10 is a flowchart illustrating an exemplary method for mapping brain function using the optical imaging system shown in FIG. 9.

FIG. 10 is a flowchart 1000 that illustrates an exemplary method for utilizing optical system 900 (shown in FIG. 9), for mapping brain function as described in greater detail above. In the exemplary embodiment, a time series of light measurements is determined 1002 by computer 902 (shown in FIG. 9). The time series is determined for a plurality of spatially distributed sources 914 and 920, and detectors 916 and 918 (each shown in FIG. 9). A subject rests or performs tasks, and the source-detector pairs receive 1004 light measurements over a period of time. Computer 902 produces 1006 one or more maps of respective strength of one or more associated temporal correlations. Specifically, processor 904 (shown in FIG. 9) produces the maps based on the time series and the received light measurements. In at least one embodiment, computer 902 receives the light measurements using at least one of planar reflectance geometry, a raster-scanning source-detector pair, and a plurality of discrete spatially distributed independent source-detector pairs.

Previous fMRI studies have demonstrated that the motor and visual cortices belong to separate functional networks, each with high levels of inter-hemispheric correlation. In addition, both regions can be located with simple task-activation paradigms. These regions thus present an ideal model system for the investigation of functional connectivity with diffuse optical tomography. Within both networks, it is expected for the resting-state analysis to produce correlation maps that highlight the same areas as were obtained with the activation studies, while the other imaging pad provides a control that should be uncorrelated.

These hypotheses are confirmed by the results of the DOT imaging. With the visual cortex seeds, we see a symmetrical activation pattern, where high correlations are seen bilaterally in the same regions as the activations occurred. The correlation maps are slightly broader than the activation maps. This may be due to the involvement of brain regions involved with higher-order visual processing; while these regions might not activate strongly with the simple checkerboard paradigm, they may still correlate strongly in the resting-state. Other interesting features in the visual cortex images are the lower correlation along the midline and the flat region of low correlation along the bottom of the imaging domain. Meanwhile, there is only the expected low correlation between the visual seeds and the motor cortex pad. These results reproduce the pattern expected from fMRI.

The differences between correlation maps determined with different hemodynamic contrasts is seen. If these differences are due to physiology, using DOT to examine the contribution of different hemoglobin species to functional connectivity could be a fruitful area of future research, helping to investigate the biophysical origin of the correlations. Similarly, the comparison of DOT correlation coefficients with those found with fMRI could be of use in this regard.

While fMRI typically uses a repetition time (TR) of about 2.5 seconds, our DOT system has a full frame rate of 10.8 Hz. This means that systemic fluctuations (e.g., pulse and breathing) are unlikely to be aliased into lower-frequency bands where the functional connectivity signal is found. So, these corrupting signals can be removed with simple low-pass filters, and do not require complicated regressions.

These results demonstrate the successful application of functional connectivity methods to diffuse optical tomography of adult human subjects. The resulting agreement with fMRI increases our confidence in the fidelity of our DOT imaging methods. These results provide a strong foundation for moving beyond where fMRI is capable of imaging. Functional connectivity has promise as a clinical tool to evaluate brain function in many populations unsuitable to standard MRI imaging. It can be contemplated to extend the analysis presented here to study questions of interest to contemporary neuroscience, in the areas of brain disease and development.

Generally, aspects of the invention include mapping brain functions with optical methods without using tasks and instead analyzing spontaneous brain activity.

There are at least four other aspects of the disclosed technology beyond the description provided above: different imaging contrasts, different optical imaging systems, different analysis schemes, and different application areas for optical imaging of functional connectivity.

Different imaging contrasts: The hemoglobin concentrations could be replaced by either cerebral blood flow assays via laser speckle measurements, diffuse correlation spectroscopy, or fluorescence measurements. In principal, cerebral blood flow is more tightly correlated with neural activity. Speckle flow and diffuse correlation measurements can be made by computing the mean and standard deviation over either spatial ensembles or temporal ensembles of speckle measurements. Either approach can be used to map or image blood flow. Using one of these speckle-flow measurement devices, one could image blood flow distributed different regions of the brain. Using the same spatio-temporal analysis outlined for hemoglobin concentration, functional connected regions could be identified. For example, in intraoperative situations, the speckle flow measures could be obtained for pre-operative surveys of brain function.

Contrast agents (via absorption, scattering, or fluorescence mechanisms) reporting either blood volume, calcium concentrations or providing sensitivity to local voltage could also be used as a fundamental optical imaging contrast. The same spatio-temporal analyses could be applied to these contrasts as described for the intrinsic hemoglobin absorption measurements analysis.

Other Analysis: Instead of using seed regions and a correlation analysis, one could use Independent Component Analysis (ICA). This approach provides a blind decomposition of the data and does not require a priori identification of seed regions. The ICA method assumes that measured signals are a weighted, linear sum of underlying independent source signals. ICA algorithms then estimate the statistically independent source component from a set of measured mixed signals by maximizing the non-Gaussianness of the estimated source signals using one of several nonlinear contrast functions as metrics.

While the ICA approach does not require seeds, it does require sorting of the resulting IC's in an embodiment. The sorting could be accomplished through analysis of the spatial components and the time series of the IC's. Networks could be identified by a two step process. First, a frequency analysis would select components that have more than 50% of the power spectrum at frequencies lower than 0.1 Hz. Secondly, a spatial template of the intended network would be constructed and a goodness-of-fit score would be calculated based on the spatial correlation between the templates and each component. Note that this template approach does not alter the components but rather ranks the components after decomposition of the data.

Exemplary application areas include: Monitoring brain function during administration of anesthesia; providing feedback for depth of anesthesia, in particular making sure the patient is not over-dosed; monitoring brain function during cardiac bypass surgery; monitoring brain function during intensive care for patients with traumatic brain injury; providing feedback during the management of cerebral blood pressure; monitoring brain function during intensive care of neonates; and providing feedback for therapeutics including brain cooling, caffeine, surfactants, and ventilation strategies. In each case the status of the brain would be monitored by identifying a set of functional networks for the patient. For continuous monitoring applications, one would monitor the strength of the functional networks over time. In addition to binary assessment (presence or absence of a functional connection), the graded strength of a network could be measured using statistical metrics such as the F-statistic approach to evaluating the robustness of a particular correlation r-value.

The functional connectivity methods for optical methods differ from those used with MRI. One critical component of getting the functional connectivity approach to perform well is pre-processing the data to remove extraneous physiological sources from the data prior to evaluating the underlying functional connections in the neuronally driven coherent spontaneous activity. For these processing steps, Optical and MRI methods differ at least in the ways next described.

Different bio-physical sources of signal. The physics are optical imaging and MRI are different. MRI contrasts derive from the magnetic permeability properties of tissues, whereas optical imaging contrasts derive from light absorption, scattering or fluorescence within tissues. In principal, both modalities use a contrast related to the dynamic concentration of deoxyhemoglobin. Functional MRI (fMRI) uses a blood oxygen level dependent signal (or fMRI-BOLD), and optical imaging can perform spectroscopy to determine deoxyhemoglobin concentration. However, these contrasts have different sampling weights across the different vascular compartments (arterial, venous and capillary). In addition, the mechanisms for coupling between neural activity and the fMRI-BOLD signal or optical contrast involve many unknown variables. Because of these uncertainties, the previously existing art has not discussed how underlying low frequency neural signals would manifest in optical approaches or how the extraneous noise sources will effect correlation mapping methods. Finally, the optical methods have oxy- and total hemoglobin contrasts which are not represented by the fMRI-BOLD signal, and thus functional connectivity methods have not been explored with these contrasts unique to optical imaging.

Field of view: MRI is fundamentally a whole brain imaging method. The whole brain field of view (full 3D) is used in the correlation analysis to remove spurious common mode signals. In contrast, optical methods are either superficial, or perhaps permit a layered (2+ dimensions) analysis. It is not obvious based on existing art that the functional connectivity methods will work with only partial, or superficial sampling.

Transmission measurements: Non-invasive optical measurements use SD-pairs involving the transmission through the scalp and skull to get to the brain. Correlation analyses could potentially be corrupted by this measurement approach. In particular, systemic sources of low-frequency oscillations might prevent the detection of low-frequency neural signals.

The non-obviousness of functional connectivity approaches in optical imaging is supported not only for the reasons outlined above, but is also reflected in lack of prior art for optical functional connectivity studies. Pre-existing optical studies that do evaluate low frequency signals have not focused on the neural origins of the low frequency optical signals or spatial mappings of brain function, but have instead focused on characterizing the systemic sources of the signal including auto-regulation, breathing, and others.

Despite these potential challenges, the exemplary embodiments of imaging systems and methods discussed above with reference to the drawings and figures demonstrate that mapping functional connectivity with optical techniques is feasible.

A computing device or computer such as described herein has one or more processors or processing units and a system memory. The computer typically has at least some form of computer readable media. Computer readable media, which include both volatile and nonvolatile media, removable and non-removable media, may be any available medium that may be accessed by computer. By way of example and not limitation, computer readable media comprise computer storage media and communication media. Computer storage media include volatile and nonvolatile, removable and non-removable media implemented in any method or technology for storage of information such as computer readable instructions, data structures, program modules or other data. For example, computer storage media include RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that may be used to store the desired information and that may be accessed by computer. Communication media typically embody computer readable instructions, data structures, program modules, or other data in a modulated data signal such as a carrier wave or other transport mechanism and include any information delivery media. Those skilled in the art are familiar with the modulated data signal, which has one or more of its characteristics set or changed in such a manner as to encode information in the signal. Wired media, such as a wired network or direct-wired connection, and wireless media, such as acoustic, RF, infrared, and other wireless media, are examples of communication media. Combinations of any of the above are also included within the scope of computer readable media.

Although described in connection with an exemplary computing system environment, embodiments of the invention are operational with numerous other general purpose or special purpose computing system environments or configurations. The computing system environment is not intended to suggest any limitation as to the scope of use or functionality of any aspect of the invention.

Embodiments of the invention may be described in the general context of computer-executable instructions, such as program modules, executed by one or more computers or other devices. The computer-executable instructions may be organized into one or more computer-executable components or modules. Generally, program modules include, but are not limited to, routines, programs, objects, components, and data structures that perform particular tasks or implement particular abstract data types. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein. Aspects of the invention may also be practiced in distributed computing environments where tasks are performed by remote processing devices that are linked through a communications network. In a distributed computing environment, program modules may be located in both local and remote computer storage media including memory storage devices.

In operation, a computer executes computer-executable instructions embodied in one or more computer-executable components stored on one or more computer-readable media to implement aspects of the invention described and/or illustrated herein.

The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for utilizing a diffuse optical tomography (DOT) system including a plurality of spatially distributed source-detector pairs for taskless mapping of brain function, the method comprising:
   determining a time series of dynamic light measurements for the plurality of spatially distributed source-detector pairs;
   receiving the dynamic light measurements over a period of time using the source-detector pairs;
   generating a plurality of temporal correlations between regions of a brain for the dynamic light measurements based on the time series of the spatially distributed source-detector pairs and the received dynamic light measurements, wherein one of the plurality of temporal correlations corresponds to one of the time series such that each time series has a corresponding correlation coefficient;
   producing at least one map of a respective strength of each of the plurality of temporal correlations; and
   producing overlapping source-detector pairs measurements using DOT geometries;
   reconstructing data representative of the dynamic light measurements into an image space using at least one DOT algorithm;
   co-registering DOT voxel images obtained by the reconstruction to anatomical information;
   determining at least one resting-state neural activity driven functional connection between a first region of the brain and a second region of the brain based on the dynamic light measurements and the plurality of temporal correlations, wherein the dynamic light measurements and the plurality of temporal correlations do not depend on either a task or a change in physiological condition.

2. The method of claim 1, wherein receiving the dynamic light measurements comprises recording fluctuations in one of light absorption, scattering fluorescence, and coherence optical contrasts.

3. The method of claim 2, wherein receiving the dynamic light measurements further comprises receiving the dynamic light measurements one of invasively and non-invasively.

4. The method of claim 3, wherein receiving the dynamic light measurements further comprises receiving one of time resolved measurements, frequency domain measurements, and continuous wave measurements.

5. The method of claim 1, wherein receiving the dynamic light measurements comprises receiving the dynamic light measurements using planar reflectance geometry.

6. The method of claim 1, wherein receiving the dynamic light measurements comprises receiving the dynamic light measurements using one of a raster-scanning source-detector pair and a plurality of discrete spatially distributed independent source-detector pairs.

7. The method of claim 1, further comprising obtaining a cortical surface image and mapping DOT voxel images obtained by the reconstruction onto the cortical surface image.

8. The method of claim 1, wherein generating the plurality of temporal correlations between regions of the brain further comprises generating the plurality of temporal correlations using a correlation analysis that is interpreted as a map of resting-state functional connections.

9. The method of claim 8, further comprising removing extraneous global correlation structures prior to mapping the resting-state functional connections.

10. The method of claim 9, wherein removing extraneous global correlation structures comprises removing the extraneous global correlation structures using one of averaged subsets of the measurements obtained by the plurality of source-detector pairs and regions of interest within an image.

11. The method of claim 10, wherein removing global correlation structures comprises removing the extraneous global correlation structures using one of physiological monitoring and signals derived from alternative imaging modalities.

12. The method of claim 1, wherein generating the plurality of temporal correlations between regions of the brain further comprises generating the plurality of temporal correlations using a correlation analysis based on a plurality of seed regions.

13. The method of claim 12, further comprising performing the correlation analysis using a comprehensive search of a plurality of voxels as seed regions, and ranking the correlated seed regions.

14. The method of claim 1, further comprising generating the plurality of temporal correlations between regions of the brain using a data-driven correlation analysis using one of a principal components analysis and an independent component analysis.

15. The method of claim 1, further comprising combining attenuation data and measurements into at least one of hemoglobin concentrations and scattering contrasts.

16. A diffuse optical tomography (DOT) system for taskless mapping of brain function, the system comprising:
 a plurality of spatially distributed source-detector pairs, the source-detector pairs configured to receive light measurements over a period of time; and
 a computer coupled to a display and to the plurality of source-detector pairs, the computer configured to:
 determine a time series of dynamic light measurements for the plurality of source-detector pairs;
 generate a plurality of temporal correlations between regions of a brain for the dynamic light measurements based on the time series of the spatially distributed source-detector pairs and the received dynamic light measurements, wherein one of the plurality of temporal correlations corresponds to one of the time series such that each time series has a corresponding correlation coefficient;
 produce at least one map of a respective strength of each of the plurality of temporal correlations; and
 produce overlapping source-detector pairs measurements using DOT geometries;
 reconstruct data representative of the dynamic light measurements into an image space using at least one DOT algorithm;
 co-register DOT voxel images obtained by the reconstruction to anatomical information;
 determine at least one resting-state neural activity driven functional connection between a first region of the brain and a second region of the brain based on the dynamic light measurements and the plurality of temporal correlations, wherein the dynamic light measurements and the plurality of temporal correlations do not depend on either a task or a change in physiological condition.

17. A computer program embodied on a non-transitory computer readable medium for taskless mapping of brain function using a diffuse optical tomography (DOT) system including a plurality of spatially distributed source-detector pairs, the computer program comprising at least one code segment that configures a processor to:
 determine a time series of dynamic light measurements for the plurality of spatially distributed source-detector pairs;
 receive dynamic light measurements over a period of time;
 generate a plurality of temporal correlations between regions of a brain for the dynamic light measurements based on the time series of the spatially distributed source-detector pairs and the received dynamic light measurements, wherein one of the plurality of temporal correlations corresponds to one of the time series such that each time series has a corresponding correlation coefficient;
 produce at least one map of a respective strength of each of the plurality of temporal correlations; and
 produce overlapping source-detector pairs measurements using DOT geometries;
 reconstruct data representative of the dynamic light measurements into an image space using at least one DOT algorithm;
 co-register DOT voxel images obtained by the reconstruction to anatomical information;
 determine at least one resting-state neural activity driven functional connection between a first region of the brain and a second region of the brain based on the dynamic light measurements and the plurality of temporal correlations, wherein the dynamic light measurements and the plurality of temporal correlations do not depend on either a task or a change in physiological condition.

* * * * *